United States Patent
Ambrose et al.

(10) Patent No.: US 12,277,099 B2
(45) Date of Patent: *Apr. 15, 2025

(54) SYSTEMS AND METHODS FOR AGGREGATING DATA RELATED TO EMPLOYEE AND PATIENT RECORDS

(71) Applicant: BLUESIGHT, INC., Alexandria, VA (US)

(72) Inventors: Rebecca Ellen Ambrose, Baltimore, MD (US); Matthew Ford, Catonsville, MD (US); Eric Southern, London (CA); Alexandra Gilliland, Baltimore, MD (US); Brian Tracey, Douglassville, PA (US); Corey O'Connor, Seattle, WA (US); Nicholas Culbertson, Baltimore, MD (US)

(73) Assignee: BLUESIGHT, INC., Alexandria, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/760,961

(22) Filed: Jul. 1, 2024

(65) Prior Publication Data

US 2024/0403279 A1 Dec. 5, 2024

Related U.S. Application Data

(63) Continuation of application No. 18/328,337, filed on Jun. 2, 2023, now Pat. No. 12,050,572.

(51) Int. Cl.
*G06F 16/21* (2019.01)
*G06F 16/215* (2019.01)
(Continued)

(52) U.S. Cl.
CPC .......... *G06F 16/219* (2019.01); *G06F 16/215* (2019.01); *G06F 16/2358* (2019.01); *G06F 16/288* (2019.01)

(58) Field of Classification Search
None
See application file for complete search history.

(56) References Cited

U.S. PATENT DOCUMENTS

2013/0304506 A1 11/2013 Gallivan et al.
2013/0325882 A1 12/2013 Deshpande et al.
(Continued)

OTHER PUBLICATIONS

International Search Report and Written Opinion issued in International Application No. PCT/US24/31651, issued Sep. 10, 2024 (11 pages).

*Primary Examiner* — Eddy Cheung
(74) *Attorney, Agent, or Firm* — Knobbe, Martens, Olson & Bear, LLP

(57) ABSTRACT

Various aspects described herein relate to systems and methods for merging records from multiple database systems. A method may include comparing, by one or more processors, two or more records of a plurality of records. The plurality of records may be from a plurality of database systems. Each of the plurality of records may be a patient record or an employee record. The method may also include determining, by the one or more processors, that a threshold match exists between the two or more records based upon a set of threshold matching criteria. The method may also include merging, by the one or more processors, the two or more records, based upon determining that the threshold match exists, into a person database entity. A unique entity identifier may be associated with the person database entity.

20 Claims, 8 Drawing Sheets

(51) Int. Cl.
*G06F 16/23* (2019.01)
*G06F 16/28* (2019.01)

(56) References Cited

U.S. PATENT DOCUMENTS

| | | |
|---|---|---|
| 2019/0088354 A1 | 3/2019 | Yanowitz et al. |
| 2019/0258731 A1 | 8/2019 | Milkhailov et al. |
| 2020/0042519 A1 | 2/2020 | Tomlin |
| 2021/0294797 A1 | 9/2021 | Gupta et al. |
| 2023/0245651 A1 | 8/2023 | Wang |

SYSTEMS AND METHODS FOR AGGREGATING DATA RELATED TO EMPLOYEE AND PATIENT RECORDS

CROSS-REFERENCE TO RELATED APPLICATION

This patent application is a continuation of and claims the benefit of priority to U.S. application Ser. No. 18/328,337, filed on Jun. 2, 2023, the entirety of which is incorporated herein by reference

TECHNICAL FIELD

The present disclosure relates generally to aggregating and consolidating data related to an individual person, such as a patient or an employee of a healthcare provider system, across multiple records or accounts spanning multiple database systems.

BACKGROUND

With the usage increase of electronic medical records in day-to-day healthcare workflows, patient medical records associated with a patient may be stored in various systems managed by different healthcare providers or groups. Even when the records associated with a patient are stored in a single system, they are often not linked or correlated with each other, making it hard to identify all relevant records for a patient. It is also common for an employee operating in a healthcare provider network to have access to multiple systems via different accounts or use multiple accounts in a single system, to enable them to perform different tasks in their typical workflow.

Unless otherwise indicated herein, the materials described in this section are not prior art to the claims in this application and are not admitted to be prior art, or suggestions of the prior art, by inclusion in this section.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In accordance with an aspect described herein a method for merging records from multiple database systems is provided. The method includes comparing, by one or more processors, two or more records of a plurality of records. The plurality of records may be from a plurality of database systems. Each of the plurality of records may be a patient record or an employee record. The method also includes determining, by the one or more processors, that a threshold match exists between the two or more records based upon a set of threshold matching criteria. The method also includes merging, by the one or more processors, the two or more records, based upon determining that the threshold match exists, into a person database entity. A unique entity identifier may be associated with the person database entity.

In yet another aspect, a non-transitory computer-readable medium storing instructions which, when executed by one or more processors, cause the one or more processors to perform operations for merging records from multiple database systems. The operations may include comparing two or more records of a plurality of records. The plurality of records may be from a plurality of database systems. Each of the plurality of records may be a patient record or an employee record. The operations may also include determining that a threshold match exists between the two or more records based upon a set of threshold matching criteria. The operations may also include merging the two or more records, based upon determining that the threshold match exists, into a person database entity. A unique entity identifier may be associated with the person database entity. The operations may further include updating, by the one or more processors at a second time, the person database entity. The updating may include at least one of adding a new record to the person database entity based upon determining that a second threshold match exists between the new record and the two or more records in the person database entity, or removing a record of the two or more records from the person database entity based upon determining that the threshold match does not exist between the record and a remainder of the two or more records.

In another aspect, a record consolidation system for consolidating and/or merging records from multiple database systems is provided. The system includes a memory storing instructions and one or more processors operatively connected to the memory and configured to execute the instructions to perform operations. The operations may include comparing two or more records of a plurality of records. The plurality of records may be from a plurality of database systems. Each of the plurality of records may be a patient record or an employee record. The operations may also include determining that a threshold match exists between the two or more records based upon a set of threshold matching criteria. The operations may also include merging the two or more records, based upon determining that the threshold match exists, into a person database entity. A unique entity identifier may be associated with the person database entity.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Figure 1:
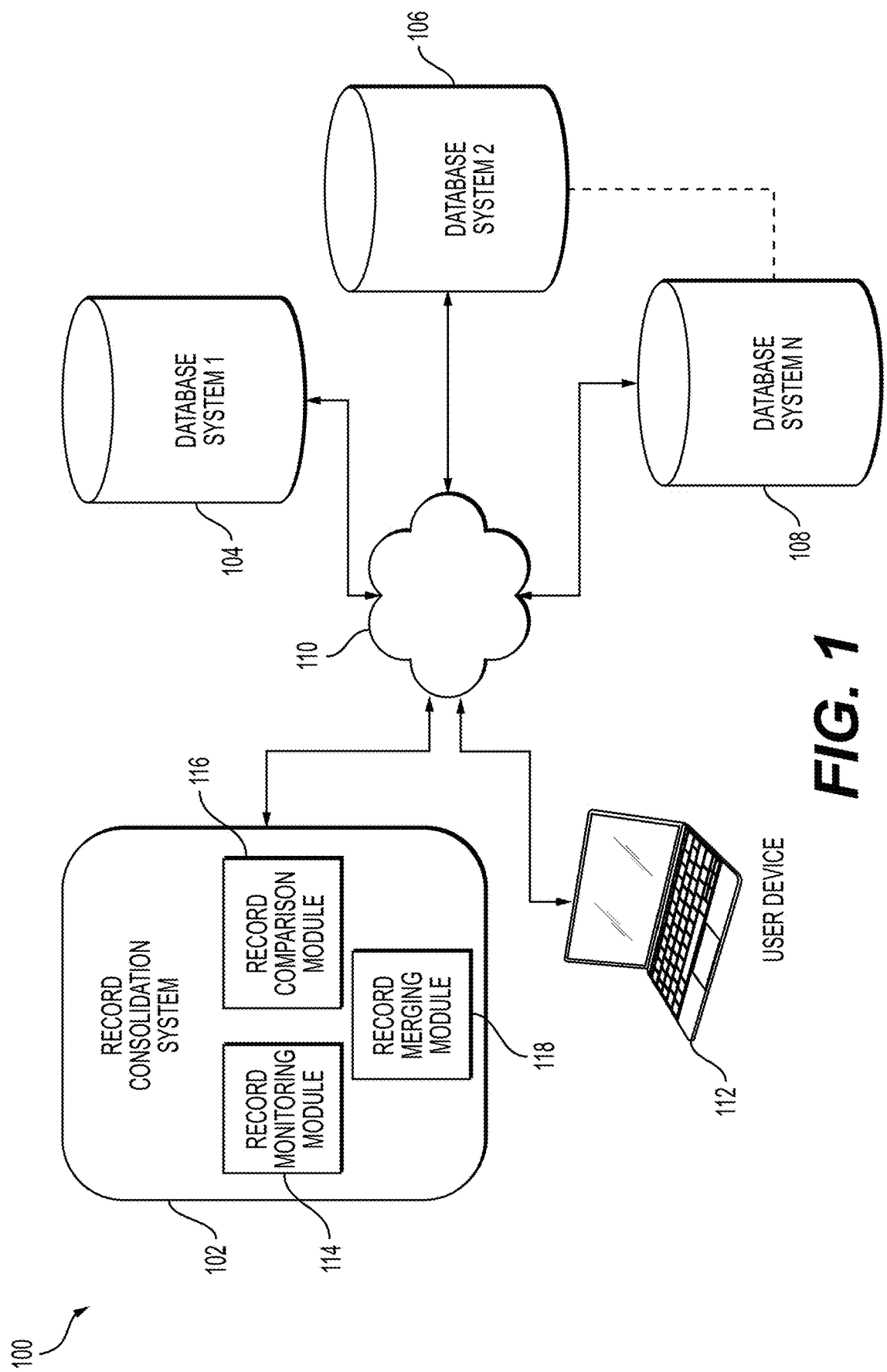
FIG. 1 illustrates an environment for merging records from multiple database systems in accordance with aspects described herein.

Aspects described herein generally relate to aggregating and consolidating data related to an individual person, such as a patient or an employee of a healthcare provider system, across multiple patient records and user accounts (e.g., employee accounts) spanning multiple data systems which contain information about the individual person. Aggregation of the data may be performed in order to associate records with the right person. Based on the consolidated records, insights may be derived about the person's behavior and risks posed by that behavior. Specifically, insights derived from the consolidated records may be more accurate and reliable since the segregated, prior data does not show the whole picture and users may be able to evade detection of inappropriate behavior by segmenting their access of patient records using different accounts.

In one specific non-limiting example, demographic information related to user accounts and patient records may be compared. In this case, all accounts and records which meet a minimum matching criteria with at least one other member of an entity set are merged into a single entity. For example, multiple user accounts may be resolved to a single user entity, multiple patient accounts may be resolved to a single patient entity, or user and patient data may be resolved to a person database entity. In some cases, a user account or a patient record may only belong to one instance of a certain type of entity. In other words, and for example, a user account may not belong to two user entities, but a user account may belong to a user entity and a person database entity. Each of these entities may be assigned a unique identifier which persists over time as various records and accounts are added to the entity, or removed. A history of changes to the person database entity, including adding or removing records and accounts from the person database entity, may be recorded and stored. Additional data may be processed without fundamentally changing the entity. It may also be possible for data changes to result in an entity being split into two or more novel entities, where the history of these changes may be recorded. Additionally, a manual override process may be incorporated which allows for external identification of two or more accounts or records which should not be incorporated into the same entity, or external identification of two or more accounts or records which should be incorporated into the same entity, regardless of match criteria.

In another specific non-limiting example, a method disclosed herein may include generating a persistent entity that may be composed of a large number of records with varying degrees of matching confidence between any two records. For example, the method allows for flexible removal and addition of records as data changes on a daily basis without disrupting the core identity of the entity. The combination of flexibility and permanence improves a typical alias identification process which operates on a snapshot of data from a given point in time. The method may therefore reconcile records and behavior within the user population and patient population and also across it. The record consolidation system may generate and store the data in a way that enables efficient traversal of a network in order to give context to user's actions. In some embodiments, machine learning may be used to aggregate behavioral, demographic, and other data across user accounts and patient records belonging to an individual entity.

Conventionally, the behavior and data of each account or record in the system is analyzed as if it were the entirety of behavior and data for that entity, at best incorporating limited aspects of other accounts belonging to the entity. However, this can lead to both under-identification of high-risk behavior, if that behavior is thinly spread across multiple accounts, and over-identification of high risk behavior, due to the absence of additional context which may have been provided by the other accounts or records.

These problems are constantly expanding as healthcare systems adopt new and increasingly domain-specific software technologies, and pose certain challenges for aggregating data related to an individual entity (e.g., patient or employee). For example, multiple medical records should be resolved as belonging to the same entity. In addition, this data should be stored in such a way that data analytics and machine learning can quickly and efficiently aggregate data for each entity.

The present disclosure solves this problem and/or other problems discussed above or elsewhere in the present disclosure, namely by improving the state of data to be analyzed by aggregating data from accounts or records stored across multiple different systems. Certain aspects of the present disclosure disclose a persistent person database entity that may be updated based on changes made to the accounts or records stored across multiple different systems. Therefore, the techniques disclosed in the present disclosure may also lead to conservation of computing resources, compared to the amount of computing resources conventionally required to retrieve and analyze user accounts or patient records scattered across multiple systems for detecting, e.g., inappropriate patient data or drug access behavior.

Because the record consolidation system of the present disclosure enables aggregation of multiple data within a single database system, the record consolidation system is advantageous over conventional employee account and patient medical record analysis tools. For instance, because the record consolidation system enables accumulation of multiple data from multiple database systems for analysis within a single system, the record consolidation system reduces required processing power, memory, and communication resources needed to facilitate retrieving and analyzing employee and patient records. Accordingly, the record consolidation system results in less data transfer and data bandwidth usage for a computer/communication system. In other words, the record consolidation system results in less required processing power and communication bandwidth in comparison to conventional systems. Additionally, in view of the foregoing, the record consolidation system may result in a more user-friendly, consistent, reliable, accurate, and efficient method for retrieving, storing, and analyzing employee and patient records.

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

As used herein, the term "determining" or "evaluating" encompasses a wide variety of actions. For example, "determining" and "evaluating" may include calculating, computing, processing, deriving, investigating, looking up (e.g., looking up in a table, a database or other data repository, or another data structure), ascertaining, and/or the like. Also, "determining," and "evaluating" may include receiving (e.g., receiving information), accessing (e.g., accessing data in a data repository), and/or the like. Also, "determining" may include resolving, selecting, choosing, establishing, and the like.

As used herein, the terms "element," "module," "component," and "system" may refer to a computer-related entity, either hardware, a combination of hardware and software, software, or software in execution. For example, a module may be, but is not limited to being, a machine-executable process running on a processor, a processor, an object, a thread of execution, a machine-executable program, and/or a computer. By way of illustration, both a process running on a server and the server may be a module or a component. One or more modules or components may reside within a process and/or thread of execution. In some implementations, a module may be localized on one computer and/or distributed among two or more computers.

Various aspects or features will be presented herein in terms of systems that may include a number of devices, components, modules, and the like. It is to be understood and appreciated that the various systems may include additional devices, components, modules, etc. and/or may not include all of the devices, components, modules, etc., discussed in connection with the figures. A combination of these approaches may also be used.

Referring to FIGS. 1-6 aspects are depicted with reference to one or more components and one or more methods that may perform the actions or functions described herein. Although the operations described below in FIGS. 4A-4C are presented in a particular order and/or as being performed by an example component, it should be understood that the ordering of the actions and the components performing the actions may be varied, depending on the implementation. Moreover, it should be understood that the following actions or functions may be performed by a specially-programmed processor, a processor executing specially-programmed software or computer-readable media, or by any other combination of a hardware component and/or a software component capable of performing the described actions or functions.

FIG. 1 is a diagram illustrating an environment 100 for merging records from multiple database systems, in accordance with one or more embodiments of the present disclosure. A record consolidation system 102 communicates with one or more other components of environment 100 across a network 110, including a user device 112 and one or more database systems 104-108. The record consolidation system 102 is connected via network 110 to first database system 104, second database system 106, and to one or more other database systems 108. Record consolidation system 102 may also be connected with user device 112. Each component of environment 100 may be located remotely from each other. For example, first database system 104 may be located remotely from second database system 106 and both first database system 104 and second database system 106 may be located remotely from all other database systems including nth database system 108.

First database system 104 may include one or more databases containing user records associated with employees for a healthcare service provider such as, for example, a hospital system, clinic, or a medical group. The first database system 104 may also include patient records including electronic medical records (EMRs) or electronic health records (EHRs). Second database system 106 may also include user records associated with employees for the healthcare service provider and may include patient records. Second database system 106 may be associated with the same healthcare service provider as the first database system 104 or it may be associated with a different healthcare service provider. In some embodiments, a system that administers first database system 104 does not have access or ability to read or write to second database system 106. Therefore, certain data contained in first database system 104 and in second database system 106 may be similar or duplicative without the respective administrative systems being aware. The data related to the patient and stored in the one or more database systems 104-108 may include, by way of example, demographics, medical history, medication and allergies, immunization status, laboratory test results, radiology images, vital signs, personal statistics like age and weight, and billing information. By way of example, the data related to an employee user and stored in the one or more database systems 104-108 may include access authorization data (e.g., login information, cryptographic keys, lists of systems the user has access to, access and activity logs, etc.), demographic and personal information, or associated users (e.g., managers or direct reports whom the user manages). Database systems 104-108 may include more than just a database or storage, but may include servers that perform computations and processes related to storage and access of patient medical records or employee user records.

In addition, electronic medical records can be used to operate or authorize operation of electronic drug dispensing systems. For example, electronic drug dispensing systems can be deployed at medical centers (e.g., on hospital floors, doctor's offices, etc.), and medical center personnel can operate the electronic drug dispensing systems to dispense certain drugs for certain patients. The electronic drug dispensing systems may dispense drugs for an identified patient based on a doctor's order accessed from an electronic medical record, and may log what drugs are dispensed for the patient, the quantity of drugs dispensed, the time/date of dispensing, etc.

The medical center personnel typically handle the drugs from the electronic drug dispensing system to the patient's location. In addition, in some cases, the medical center personnel may "waste" drugs, which can refer to a process of accounting for unused or mishandled drugs, that are to be disposed of. This process of "wasting" typically requires a witness to sign or acknowledge the "wasting." There are many points of potential misappropriation of drugs obtained from electronic drug dispensing systems.

By way of example, an employee of a healthcare service provider may be a user of several different accounts with various systems (e.g., database systems 104-108) that the healthcare service provider uses. The employee user may access database systems 104-108 via user device 112. Healthcare service providers may use the various systems, as supported by the database systems 104-108, to perform administrative functions, track patient records, medical history, and medical visits, store patient information, dispense drugs and other medications, book and remind patients of upcoming visits, interact with patients online, diagnose medical conditions, generate and transmit electronic prescriptions, automate daily operations, and manage billing, documentation, and inventory. In some cases, many of these functions may be performed by a single system with a centralized account and login for employees. However, in many cases, an employee may need several accounts with several different systems in order to perform basic job duties. Determining possible anomalous activity including inappropriate accessing (also referred to herein as "breach") of the data contained in these systems or misappropriation of drugs (e.g., drug diversion) may be a manual or an automated process based on analysis of the data. Data may be collected from one or more of these various systems and analyzed to determine possible breaches. For example, the collected data can include electronic patient data (e.g., from an EMR), data related to accessing the electronic patient data (e.g., an identifier of an employee accessing the EMR data, a time of accessing the EMR data, etc.), and data from an electronic drug dispensing system (e.g., dispensing data such as time of dispensing, amount of dispensing, type of drug dispensed, wasting activity, an identifier of an employee dispensing the drug, etc.). The data may also include human resources (HR) data that can indicate information related to the employees accessing the electronic patient data and/or dispensing the drugs. The collected data can be analyzed to detect whether one or more accesses of the data may possibly be a breach of the data, whether one or more drug dispensing activities may be for inappropriate purposes, etc. If possible breach or misappropriation is detected, one or more alerts can be generated (e.g., to one or more interfaces) for further investigation as to whether the access/dispensing is inappropriate given additional context around the access/dispensing. Moreover, though EMR data is generally referred to herein, the concepts described can be applied to substantially any electronically stored patient data. The techniques disclosed herein in connection with detecting patient privacy breaches may also be applicable in detecting drug diversion activity.

Record consolidation system 102 includes record monitoring module 114, a record comparison module 116, and a record merging module 118. Record consolidation system 102 may have read-write access or read-only access to some or all of the database systems 104-108. Record consolidation system may retrieve data from each database system in order to consolidate the records stored in each database system, according to one or more embodiments of the present disclosure.

Record monitoring module 114 may monitor database systems 104-108 on a regular and/or continuous basis. As used herein, the terms "regular," "on a regular basis" and "regularly" may refer to weekly, daily, multiple times per day, etc. In some embodiments, record monitoring module 114 monitors the database systems 104-108 to determine whether a new record is added, whether a record has been removed, or whether a record has been updated in database systems 104-108. In some embodiments, record monitoring module 114 compares a current number of records in each database system to a previously recorded number of records in each database system. If the number is different, record monitoring module 114 determines that a change (e.g., addition, deletion, or update) has occurred in the respective database system. In some embodiments, record monitoring module 114 may compare a previously captured snapshot of a database in database systems 104-108 with a current snapshot of the same database in database systems 104-108 to determine whether changes were made. In one or more further embodiments, record monitoring module 114 may track queries to the database systems that may change the databases contained therein. In yet further embodiments, record monitoring module may receive alerts whenever a database system is updated or changed, the alert including information relating to new, updated, or deleted entries in the database systems.

Record comparison module 116 may compare one or more records with one or more other records to determine whether the compared records match. If a match between two or more records is determined, record merging module 118 may merge the two or more records together into a person database entity, storing a history of the merge in the person database entity.

The user device 112 is configured to enable a user to access database systems 104-108. In some examples, the user may be an employee of a healthcare service provider, such as a physician, physician's assistant (PA), nurse, nurse practitioner, receptionist, certified nursing assistant (CNA), medial assistant, or anybody else who may have a reason to access a patient record. The user may use the user device 112 to record or access information related to a patient stored in database systems 104-108. The user device 112 is a computer system such as, for example, a desktop computer, a laptop computer, a tablet, a smart cellular phone, a smart watch, or other wearable computer, etc. The user device 112 includes one or more applications, e.g., a program, plugin, browser extension, etc., installed on a memory of the user device 112. The applications can include one or more of system control software, system monitoring software, software development tools, etc.

In some embodiments, at least one of the applications is associated with and configured to communicate with one or more of the other components in the environment 100, such as one or more of the database systems 104-108. For example, the at least one application may be executed on the user device 112 to communicate with the database systems 104-108.

The network 110 over which the one or more components of the environment 100 communicate includes one or more wired and/or wireless networks, such as a wide area network ("WAN"), a local area network ("LAN"), personal area network ("PAN"), a cellular network (e.g., a 3G network, a 4G network, a 5G network, etc.) or the like. In some embodiments, the network 110 includes the Internet, and information and data provided between various systems occurs online. "Online" means connecting to or accessing source data or information from a location remote from other devices or networks coupled to the Internet. Alternatively, "online" refers to connecting or accessing a network (wired or wireless) via a mobile communications network or device. The user device 112, record consolidation system 102, and the one or more of the database systems 104-108 are connected via the network 110, using one or more standard communication protocols. The user device 112, the record consolidation system 102, and the one or more database systems 104-108 transmit and receive communications from each other across the network 110.

Although depicted as separate components in FIG. 1, it should be understood that a component or portion of a component in the environment 100 is, in some embodiments, integrated with or incorporated into one or more other components. As one example, the record comparison module 116 and the record merging module 118 may be integrated into a single component or sub-system of the record consolidation system 102. In some embodiments, operations or aspects of one or more of the components discussed above are distributed amongst one or more other components. Any suitable arrangement and/or integration of the various systems and devices of the environment 100 may be used.

In the following disclosure, various acts are described as performed or executed by a component from FIG. 1, such as the user device 112 or the record consolidation system 102, or components thereof. However, it should be understood that in various aspects, various components of the environment 100 discussed above execute instructions or perform acts including the acts discussed below. An act performed by a device is considered to be performed by a processor, actuator, or the like associated with that device. Further, it should be understood that in various embodiments, various steps can be added, omitted, and/or rearranged in any suitable manner.

Figure 2:
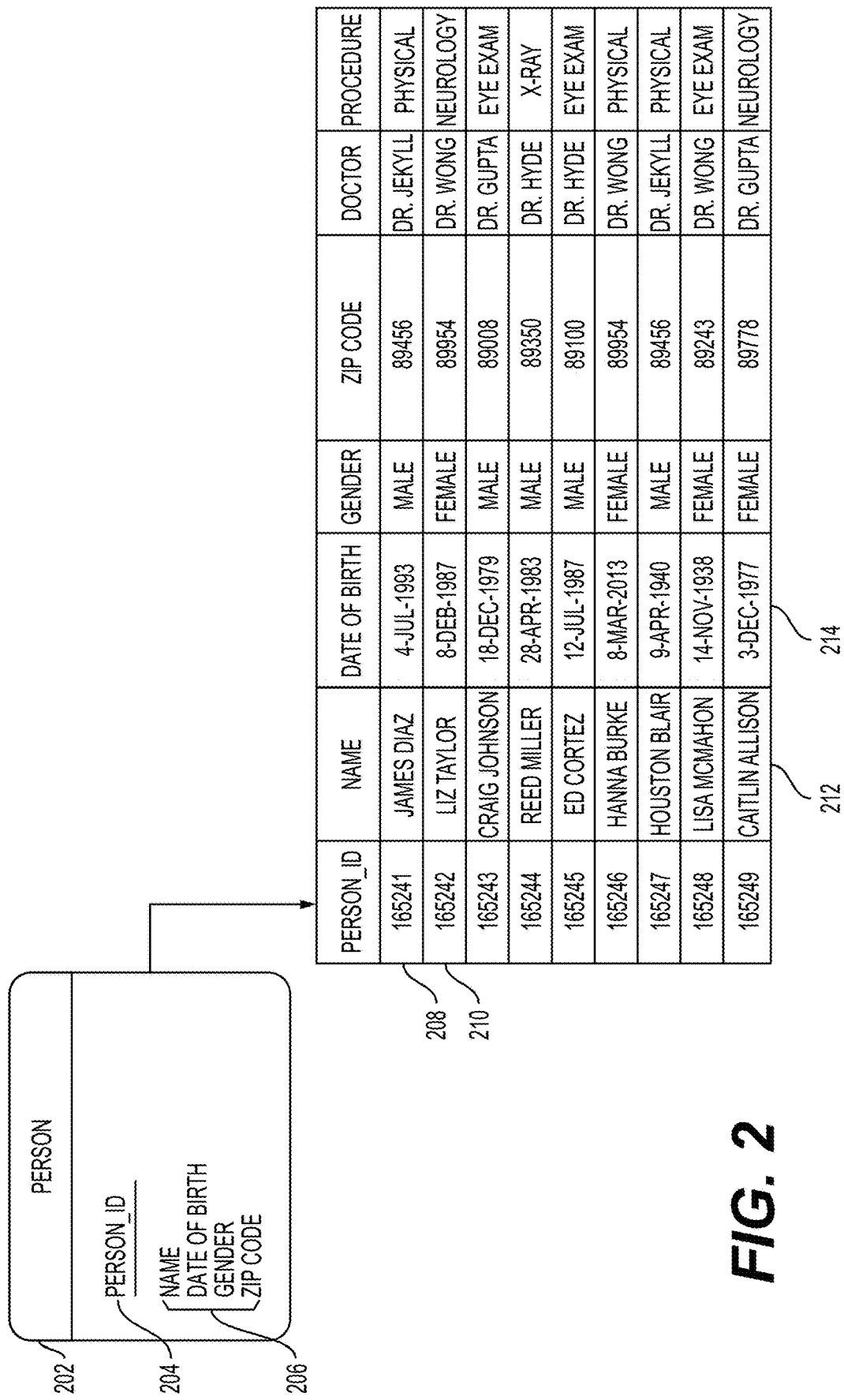
FIG. 2 illustrates an example database table and person record in accordance with aspects described herein.

FIG. 2 is a diagram illustrating an example database table 200 and person record 202, in accordance with one or more embodiments of the present disclosure. Database table 200 may include several person records, such as person record 202. Each person record includes multiple points of data related to a person associated with the record, including demographic data and medical visit history. While FIG. 2 depicts patient records, the principles discussed with relation to FIG. 2 apply equally to employee user records. Each person record may be represented by a single row of database table 200, including, for example rows 208 and 210. For example, person record represented at table row 208 includes data related to a physical examination for a person named James Diaz. The person record at row 208 may include demographic information for James Diaz, such as date of birth, gender, and zip code, as well as the name of the doctor that James Diaz visited for the physical examination. In another non-limiting example, a person record at row 210 includes data related to a neurology visit for Liz Taylor. Similar to person record at row 208, person record at row 210 includes demographic information for Liz Taylor and the name of the doctor that saw Liz Taylor for her neurology visit. Each of the person records at rows 208 and 210 also includes a record identifier PERSON_ID that may be used to identify and differentiate the record from other records in the particular database table 200.

Database table 200 includes columns such as, for example, column 212 and column 214. Names of patients associated with each record are represented in column 212. Dates of birth of patients associated with each record in database table 200 are represented in column 214. Database table 200 may be sorted according to data contained in each of the columns.

Person record 202 is a generic example of the individual data fields that may be stored in each record of database table 200. For example, person record 202 may include a record identifier 204 that is used to identify each record. In some embodiments, each person record representing a patient record corresponds to a particular visit to the healthcare service provider. Accordingly, in some cases, a single individual person may have many records in the database table 200, which each correspond to individual visits to one or more doctors within the healthcare service provider. Person record 202 may also include identifying and demographic information 206 such as, for example, name, date of birth, gender, and zip code. Even though not shown, additional demographic indicators may be included in each person record of database table 200.

Some healthcare service providers and its associated systems may maintain their own database table, such as database table 200. In some cases, a healthcare service provider and its associated system may combine individual records, such that an individual person corresponds to only one person record, and where each person record may include one or more procedures and visits to the doctor.

Figure 3:
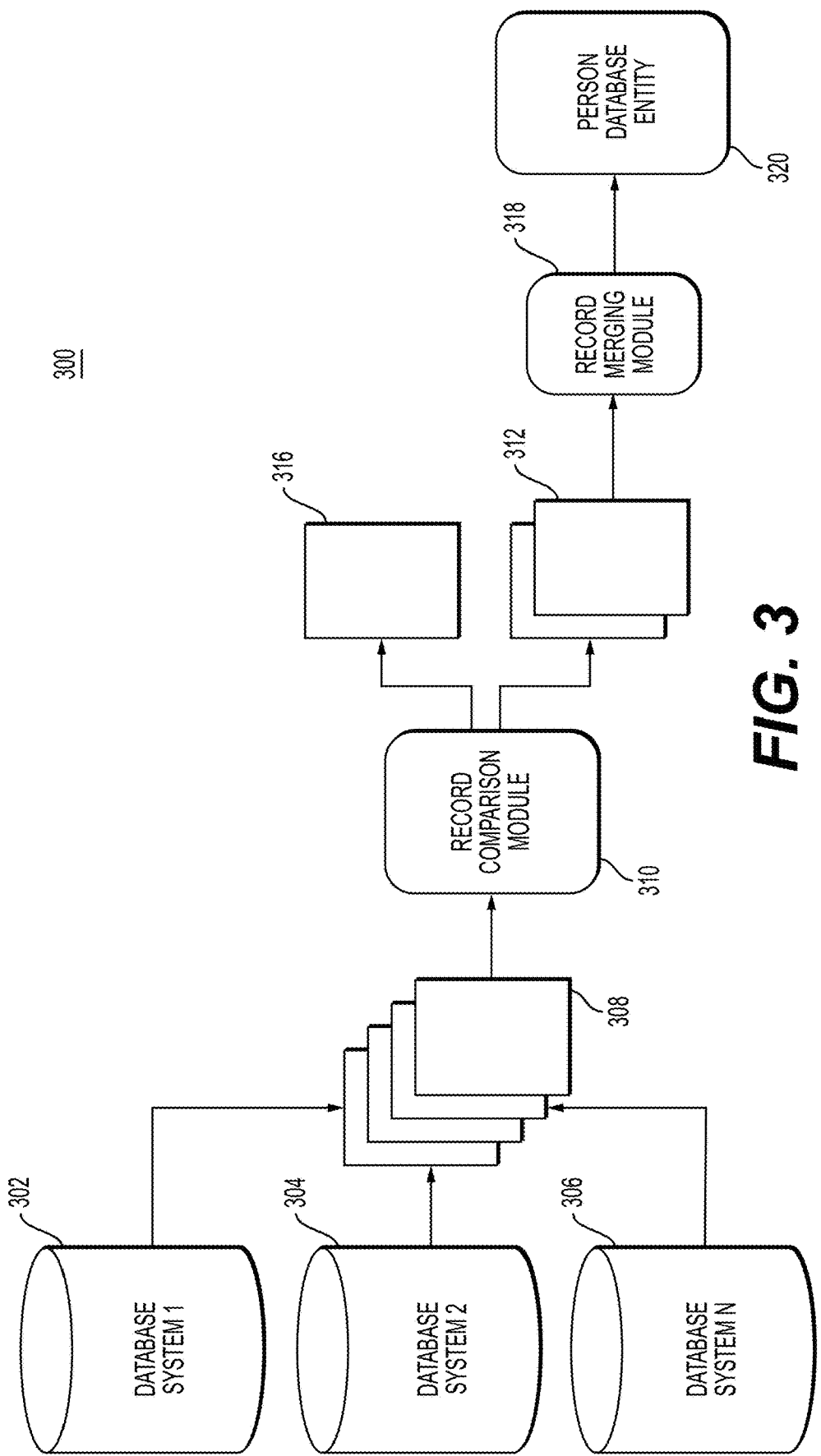
FIG. 3 illustrates an example record consolidation system for merging records from multiple database systems in accordance with aspects described herein.

FIG. 3 is a block diagram depicting an example record consolidation system 300 for merging records from multiple database systems, according to one or more embodiments of the present disclosure. Record comparison module 310 and record merging module 318 may be examples of record comparison module 116 and record merging module 118 of FIG. 1, respectively.

Records 308 may be compiled from various database systems, including first database system 302, second database system 304, and so forth until nth database system 306. Records 308 may be compiled on a regular basis and may be updated (e.g., compiled again) regularly. Records 308 may be patient records or employee user records. Records 308 may be compiled into a single database (not shown). In one or more examples, the record consolidation system 300 may query one or more database systems including first database system 302, second database system 304, until nth database system 306 to retrieve (e.g., extract, obtain) patient and employee user records. In most cases, the query may be automatic and performed on a regular basis, but the database of records 308 may be updated manually if desired.

Record comparison module 310 may receive records 308 for comparison. In some embodiments, record comparison module 310 may compare each record to every other record of records 308 to determine whether a match exists between the compared record and any other records. Record comparison module 310 may first compare a record with records from different database systems, since it is less likely that a duplicate for the record is generated within its own respective database system. If desired, a comparison may also be made with all other records contained within the same database system. In some embodiments, record comparison module 310 may determine which records of the records 308 are newly updated or added since the last comparison was executed. In this case, only the newly updated or added records may be compared to all other records. Record comparison module 310 may be configured to compare more than two records at a time.

Record comparison module 310 may output results of one or more comparisons between one or more records from records 308. The results may include, for example, a single record 316 that does not match with any other records from records 308. By way of example, this record may belong to a patient that has only visited a doctor within the particular healthcare service provider once. The results of record comparison module 310 may also include two or more records 312 that match each other, and may be considered to be representative a single individual person. In some embodiments, the output of record comparison module 310 is a list of record identifiers indicating which records were determined to be matches. The two or more records 312 that match each other are provided to a record merging module 318 for merging.

Record merging module 318 may receive the two or more matching records from the record comparison module 310. Record merging module 318 may combine the two or more records 312 into a single person database entity 320. In the embodiments where a list of matching records is output from record comparison module 310 instead of the records themselves, record merging module 318 may query the matching records' respective database systems to retrieve the records for merging. In one or more embodiments, the record merging module 318 may query the database storing records 308 that were aggregated for comparison by record comparison module 310.

A person database entity 320 may be associated with a set of two or more records pertaining to a single person. The single person associated with the person database entity 320 may be a patient. In this case, the set of records that are associated with the person database entity 320 may be patient medical records associated with the single person. In other embodiments, the single person associated with the person database entity 320 may be an employee of a healthcare service provider and the set of records that are associated with the person database entity 320 may be employee records or employee user access records. In some embodiments, the single person associated with the person database entity 320 may be a patient and an employee of the associated healthcare service provider, and the set of records associated with the person database entity 320 may include at least one patient record and at least one employee record. In some embodiments where only patients form the contents of person database entity 320, person database entity 320 may be considered a patient database entity. In embodiments where only employee users form the contents of person database entity 320, person database entity 320 may be considered a user database entity. While a patient database entity and a user database entity may be different (e.g., contain different types of records, contain different fields, or be stored in different database systems), for the purposes of this disclosure, a patient database entity and a user database entity may each be considered a person database entity. The methods discussed in the present disclosure apply to patient database entities, user database entities, and person database entities. Further, as used herein, the term "person" may refer to a patient or an employee user.

In some embodiments, a reference record may be created as representative of a newly created person database entity 320. The reference record may include some or all of the common features of the two or more records that are merged into the person database entity 320. For example, the reference record may include a name, demographic data of the associated individual, and information related to the medical visits. The reference record may also include an additional field, not typically included in records 308 retrieved from database systems 302-306, including each record identifier that comprises the two or more matching records contained in the person database entity 320. The reference record may be used for purposes of comparison with other records from records 308, such that record comparison module 310 does not duplicate comparisons. In such embodiments, record comparison module 310 may not compare new or updated records from records 308 with all other records from each of the database systems 302-306, as discussed above, but may only compare new or updated records with reference records that represent the person database entity 320. In some embodiments, the reference record may also include an additional field containing a history of changes and merges related to the person database entity.

The person database entity 320 may be analyzed on a regular basis using a machine learning model to detect anomalous activity, including unauthorized access of patient data and breaches of patient privacy. The person database entity 320 may also be analyzed regularly to detect any drug diversion activity by employees or patients.

Figure 4A:
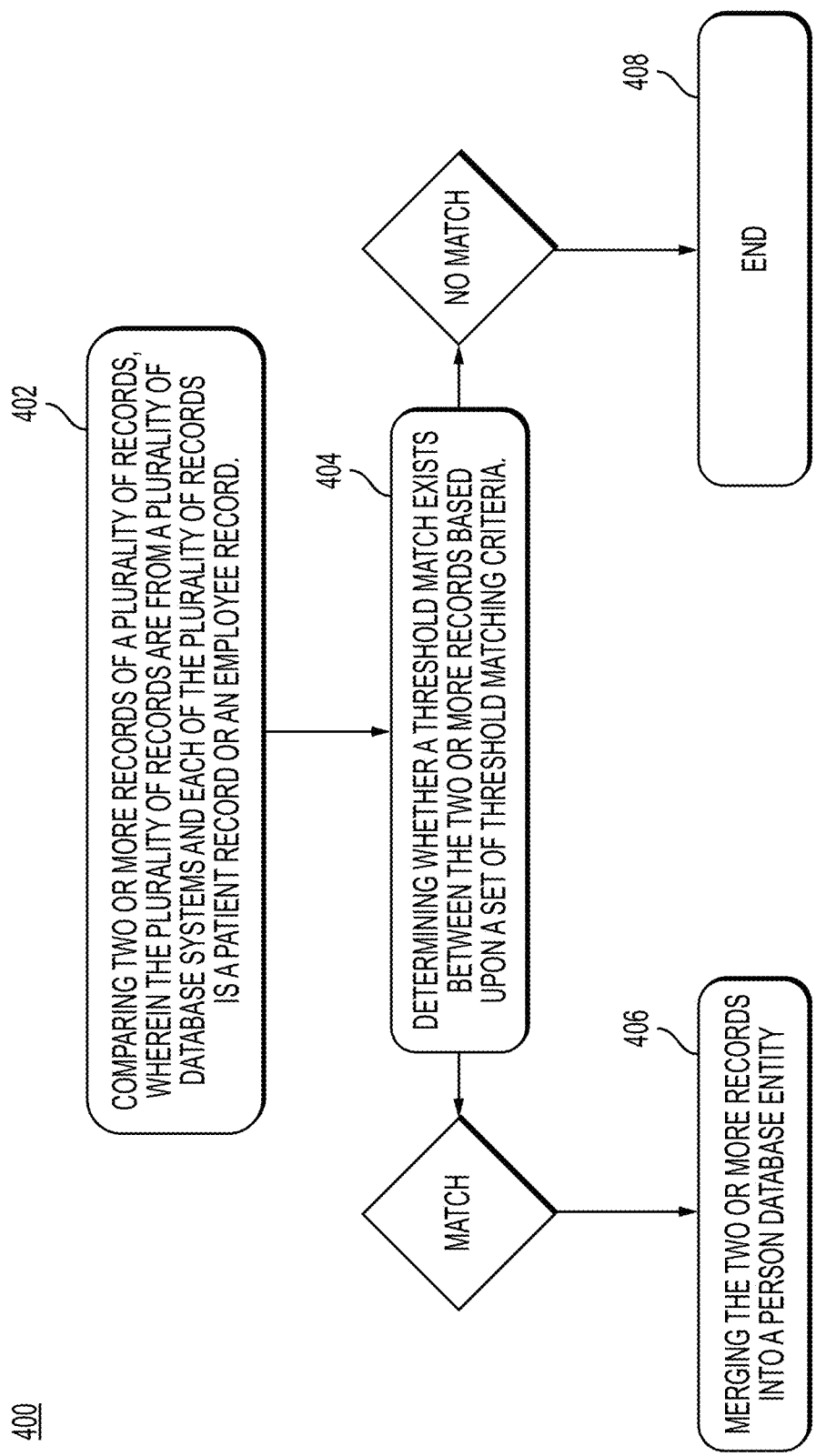
FIG. 4A illustrates an example method for merging records from multiple database systems in accordance with aspects described herein.

FIG. 4A is a flowchart depicting an example method 400 for merging records from multiple database systems, according to some embodiments of the present disclosure. Methods 400, 420, and 440 of FIGS. 4A-4C may be performed by one or more components of the record consolidation system 102 of FIG. 1, according to some embodiments of the disclosure.

At step 402, the method 400 includes comparing two or more records of a plurality of records, wherein the plurality of records are from a plurality of database systems and each of the plurality of records is a patient record or an employee record. The plurality of database systems may be examples of database systems 104-108 of FIG. 1 or database systems 302-306 of FIG. 3. The plurality of records may be an example of records 308 of FIG. 3. Step 402 may be performed, for example, by record comparison module 116 of FIG. 1. Each record of the two or more records may include one or more data points of demographic information related to the individual to whom the record pertains. When comparing the two or more records, the one or more data points of demographic information may be compared. The points of demographic information that may be compared include a name, date of birth, ethnicity, gender, sex, race, home or work address, phone number, email address, insurance information, preferred language, social security number, and medical/health data. Other non-demographic information may be compared as well including activity consistency across different systems. For example, if a particular employee has accessed each record of the two or more records (e.g., within a predefined time period), this may be an indication that the two or more records belong to the same individual (e.g., patient).

At step 404, the method 400 includes determining whether a threshold match exists between the two or more records based upon a set of threshold matching criteria. The set of threshold matching criteria may be predetermined ahead of time. In some embodiments, the set of threshold matching criteria may evolve over time as the system learns how to better match records using a pre-trained machine learning model. The set of threshold criteria may include a number of one or more types or data points of demographic information that may be used to determine the threshold match at a particular confidence rate.

By way of non-limiting example, the set of threshold criteria may include two points of demographic information such as a name and a date of birth. In this instance, if two records include the same name and date of birth, a threshold match may be determined to exist, even if no other demographic information match between the two records. The confidence rate for this set of threshold criteria may be lower than the confidence rate would be for an example set of threshold criteria that included name, date of birth, ethnicity, gender, home address, zip code, phone number, and email address. In other words, a set of threshold criteria that includes more points of demographic information may have a higher confidence rate. However, each type of demographic information used for a threshold criteria may be assigned a weight for the confidence rate. For example, name and date of birth may have a greater weight for confidence rate than gender or zip code because names and dates of birth are more unique and are less likely to be shared among multiple people than gender and zip code, which may be shared by a large amount of people. However, the overall confidence rate may be increased by including gender and zip code in addition to name and date of birth in the set of threshold criteria, due to the possibility that a person shares a name and date of birth with another, but is of a different gender or lives in a different zip code area. For example, it is possible that a healthcare service provider employs two people with the same or similar name and date of birth, but one is male and the other is female. If the threshold criteria only included name and date of birth, the records pertaining to both people may be incorrectly merged together. But if the threshold criteria included the gender, the record consolidation system would correctly differentiate between the two, and would not improperly merge their records.

Record consolidation system 102 may be configured to account for mistakes in the data, including misspellings of names and slight differences in dates of birth or addresses. In other words, records that are associated with the same individual may include minor mistakes as a result of data entry or modification, and a threshold match may still exist even with these minor mistakes.

At step 406, the method 400 includes merging the two or more records into a person database entity. Merging the two or more records into a person database entity may include creating a new person database entity and adding the two or more records into the newly created person database entity. Additionally, in some embodiments, merging the two or more records into a person database entity may include creating a reference record. The reference record may include matching demographic data contained in the compared two or more records, and may include a field including a list of record identifiers indicating which records have been merged together into the person database entity. If there are differences between the two or more records, record merging module 118 may determine which demographic information to include in the reference record. In some embodiments, the demographic information of the most recently updated record of the two or more records may be included in the reference record. In other embodiments, record merging module 118 may randomly determine which demographic information to include in the reference record. In yet other embodiments, record merging module 118 may determine which demographic information to include in the reference record based on one or more rules defined for such determination. Record merging module 118 may also create a combination of the demographic information. In some cases, all variations of the demographic information may be stored, and in some cases, one of the two or more records may be stored as the reference record without including any of the mismatching information. A history of changes to the person database entity, including a history of merges, may be stored in the person database entity, in some cases as metadata.

At step 408, upon determining that a threshold match does not exist between the two or more records, the method 400 ends and takes no further actions. In some cases, the history of changes may include a list of records that are determined not to be matches, such that future comparisons between the same records are avoided.

Figure 4B:
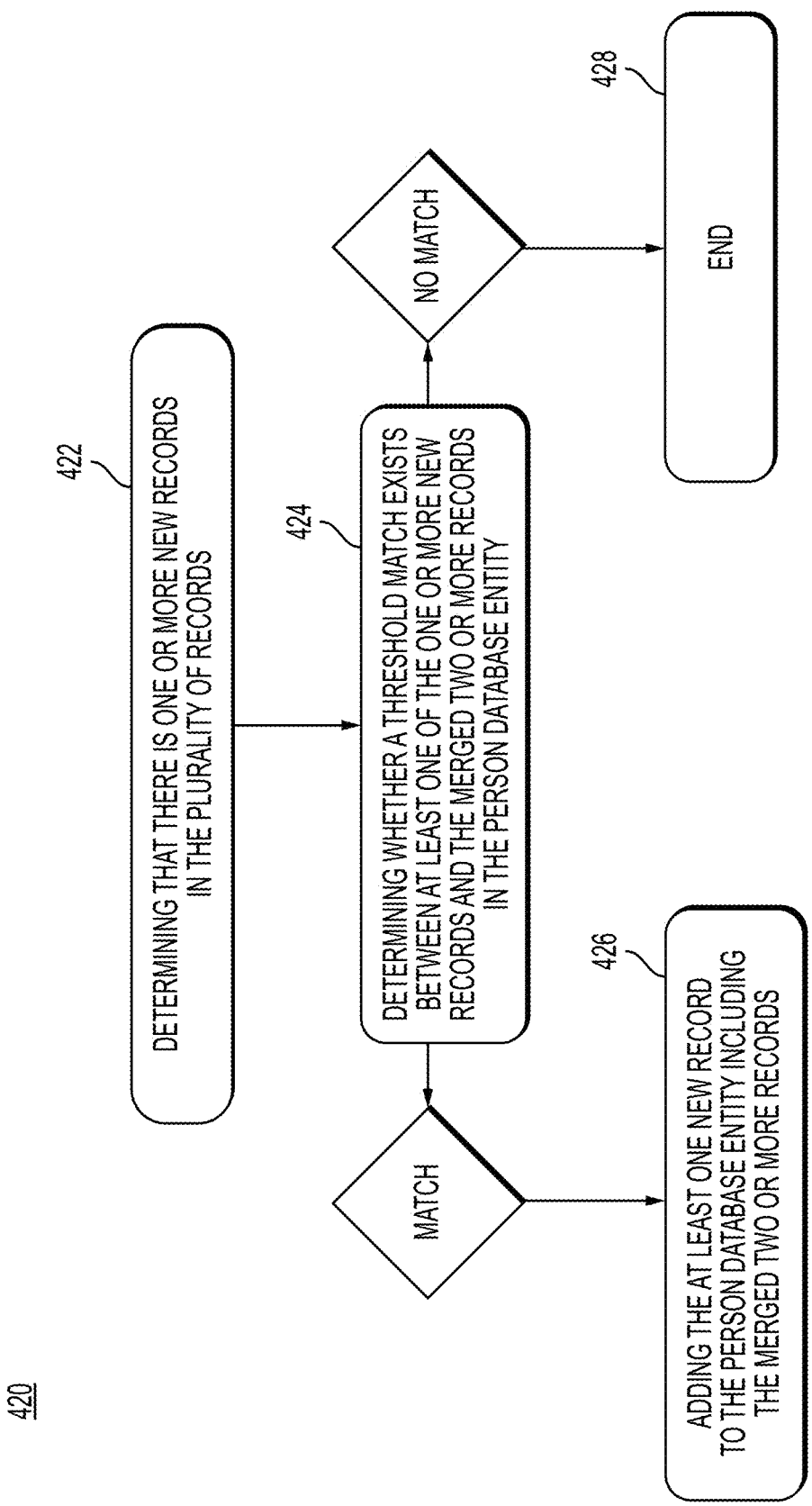
FIG. 4B illustrates an example method for adding a new record to a person database entity by the record consolidation system in accordance with aspects described herein.

FIG. 4B is a flowchart depicting an example method 420 for adding a new record to a person database entity by the record consolidation system, in accordance with embodiments of the present disclosure.

At step 422, method 420 includes determining that there is one or more new records in the plurality of records. In some embodiments, record monitoring module 114 of FIG. 1 monitors the database systems 104-108 of FIG. 1 on a regular basis to determine whether a new record is added to the database systems 104-108.

At step 424, the method 420 includes determining whether a threshold match exists between at least one of the one or more new records and the merged two or more records in the person database entity. In some embodiments of the present disclosure, the at least one new record may be compared in turn to each of the two or more records in the person database entity and a threshold match may be determined to exist with each of the records of the person database entity. If a threshold match exists between the at least one new record and a threshold number (e.g., one, all, more than 50%, or more than some other predefined percentage or number of records) of the two or more records in the person database entity, then an overall threshold match may exist between the at least one new record and the person database entity. If a threshold match exists between the at least one new record and less than the threshold number of the two or more records in the person database entity, then record comparison module 116 may determine that there is no overall threshold match between the at least one new record and the person database entity. In the embodiment where the person database entity is represented by a single reference record, the at least one new record is compared with the reference record to determine whether a threshold match exists.

At step 426, upon determining that a threshold match exists between the at least one new record and the merged two or more records in the person database entity, method 420 includes adding the at least one new record to the person database entity including the merged two or more records. In some embodiments, the record identifier of the at least one new record may be added to the reference record representing the person database entity.

At step 428, upon determining there is no match between at least one of the one or more new records and the merged two or more records in the person database entity, the method 420 ends and does not take further action.

Figure 4C:
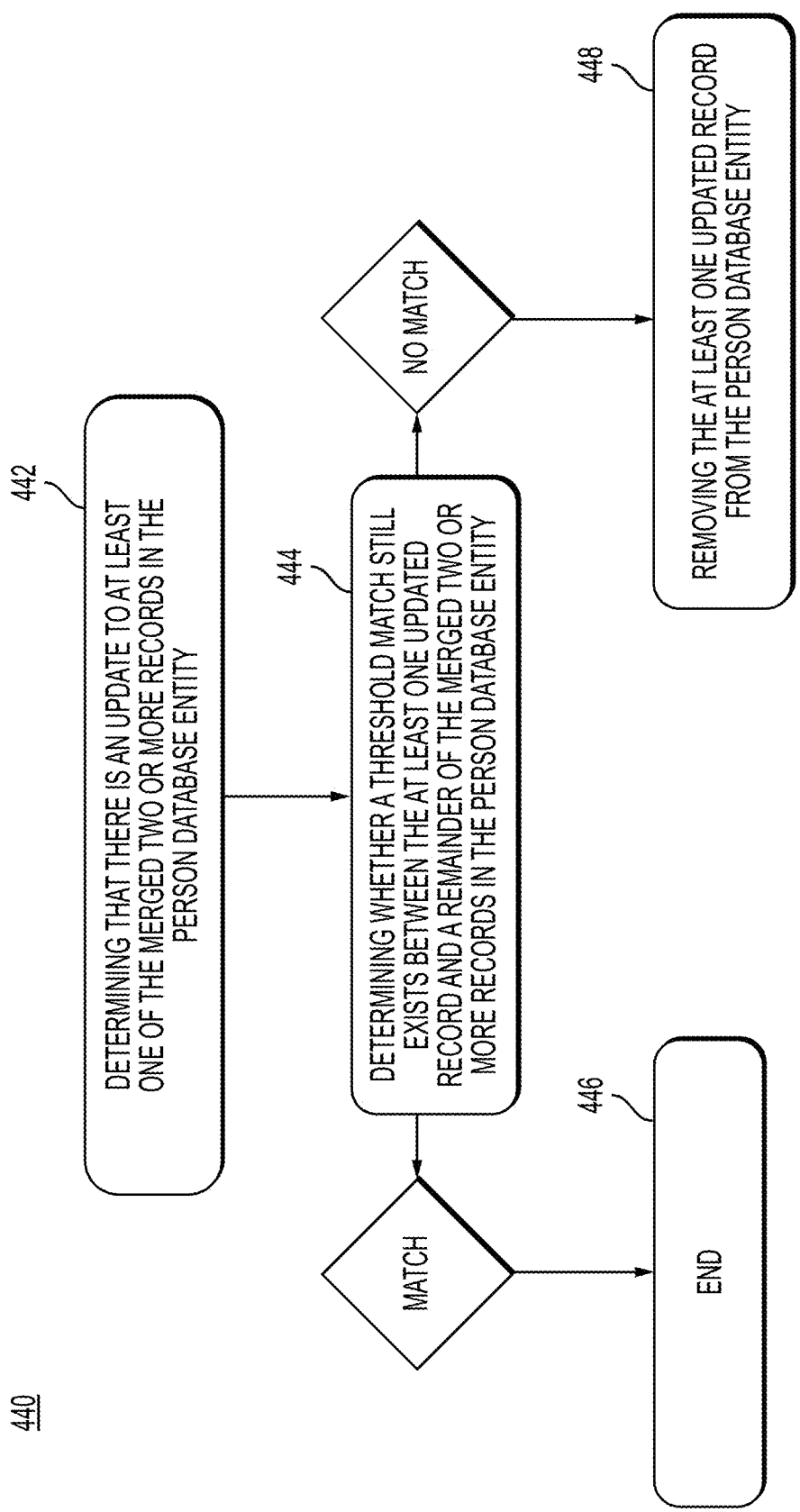
FIG. 4C illustrates an example method for removing an updated record from a person database entity in accordance with aspects described herein.

FIG. 4C is a flowchart illustrating an example method 440 for removing an updated record from the person database entity, according to one or more embodiments of the present disclosure.

At step 442, the method 440 includes determining that there is an update to at least one of the merged two or more records in the person database entity. Record monitoring module 114 may monitor the database systems 104-108 to determine changes in records stored in the database systems, in accordance with methods discussed in the present disclosure. If an update has occurred in at least one of the merged two or more records in a person database entity, the method 440 proceeds to step 444.

At step 444, the method 440 includes determining whether a threshold match still exists between the at least one updated record and a remainder of the merged two or more records in the person database entity. Determining the threshold match between the updated record the remainder of the records in the person database entity may be performed similarly as the determining step 424 of FIG. 4B.

At step 446, upon determining that there is still a threshold match between the least one updated record and a remainder of the merged two or more records in the person database entity, the method 440 ends and no further actions are taken.

At step 448, upon determining that a threshold match does not exist between the at least one updated record and remainder of the merged two or more records in the person database entity, the method 440 includes removing the at least one updated record from the person database entity. This may include querying the database that contains the person database entity to remove the at least one updated record from the person database entity. In some embodiments, a new person database entity may be created from the at least one updated record. In further embodiments, the person database entity may be deleted and two new person database entities may be created from the records previously contained in the deleted person database entity. In this instance, the history of these changes may be recorded in each new person database entity. In the embodiments related to a reference record, the system may update the field containing the record identifiers associated with the person database entity, such that the record identifier associated with the at least one updated record is removed from the field.

A manual override process may be incorporated into methods 400, 420, and 440 which allows for external (e.g., manual) identification of two or more accounts or records which should be merged into a single person database entity, regardless of whether the threshold match criteria are met. Additionally, a manual override process may be incorporated which allows for external identification of two or more accounts that have been merged based on a threshold match, but should not be merged and may therefore be unmerged. In one or more embodiments, a graphical user interface (GUI) may be displayed on a computing device of a user for manually updating the person database entity. The GUI may enable a user to perform the manual override process discussed herein by enabling the user to select records that should or should not be merged. The identification of records that should or should not be merged may be recorded by the record consolidation system 102 (e.g., record comparison module 116) as a "rule," such that the rule remains applicable during subsequent operations. The record consolidation system 102 may also allow users to modify or delete rules previously set during a manual override process, via one or more graphical elements of the GUI. The GUI may further enable a user to add a new record to person database entity using one or more graphical elements of the GUI. The GUI may also enable a user to remove a record of the two or more records from a person database entity using one or more graphical elements of the GUI. In some embodiments, the graphical elements used to add a new record to the person database entity may be the same or may be different than the graphical elements used to remove a record from the person database entity.

Figure 5:
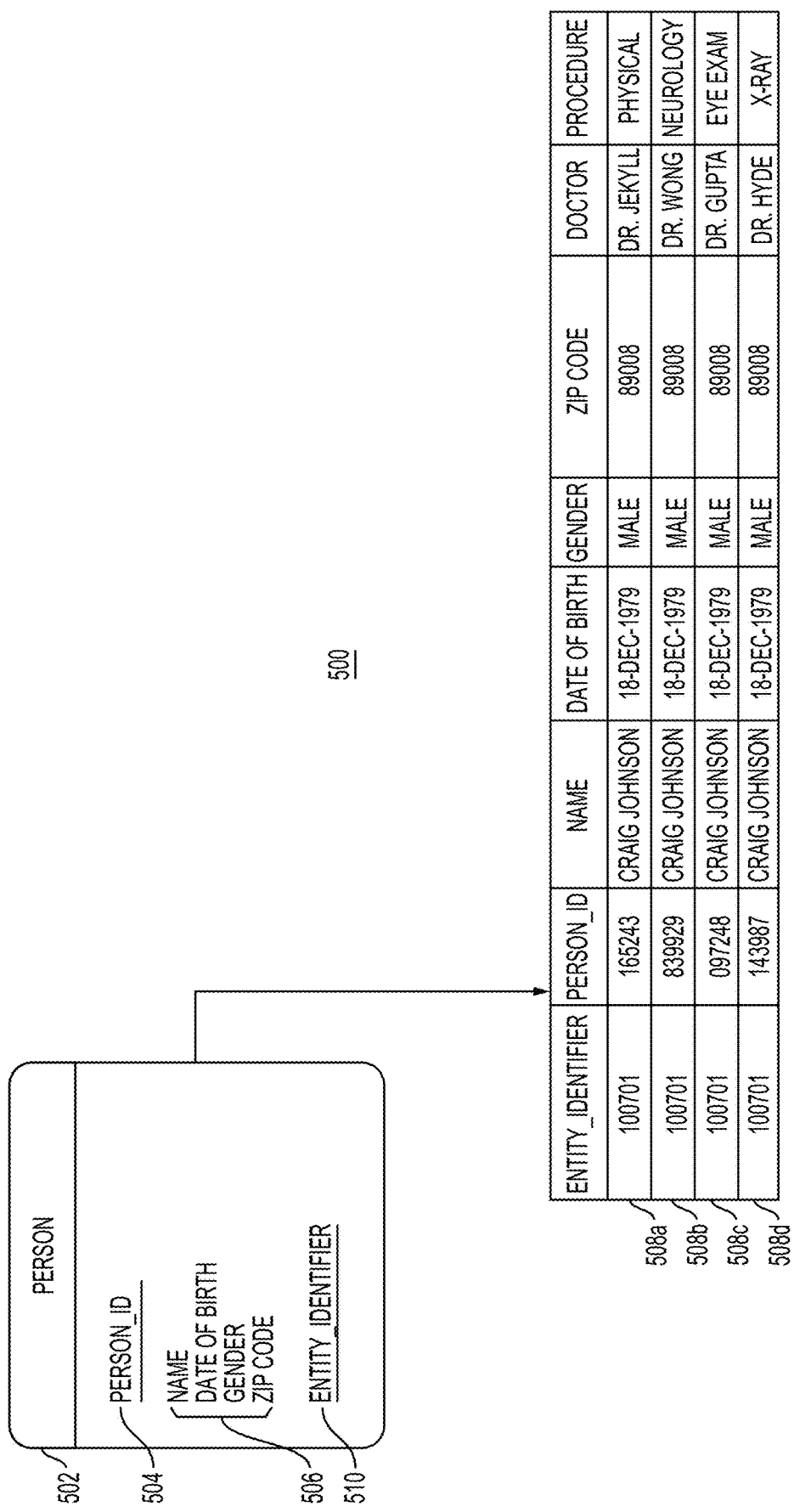
FIG. 5 illustrates an example person database entity into which a plurality of person records are merged in accordance with aspects described herein.

FIG. 5 is a diagram depicting an example person database entity 500 into which a plurality of patient records is merged, in accordance with embodiments of the present disclosure. As discussed above, person database entity 500 effectively consolidates records associated with a person that are stored across a plurality of database systems. Similar to the database table 200 of FIG. 2, which may include several person records, database entity 500 may include several person records, such as person records represented at rows 508a-508d, and represented by example person record 502. Person record 502 may differ from person record 202 of FIG. 2 due to the addition of a unique person database entity identifier 510, labeled ENTITY_IDENTIFIER. Person record 502 includes a record identifier 504, labeled PERSON_ID, which is unique to each record. Person database entity identifier 510 is assigned to the person database entity 500 and shared among all the person records within the person database entity 500, but is unique from other person database entity identifiers. Further, person database entity identifier 510 facilitates access to the person database entity by a plurality of platforms, each of the plurality of platforms configured to analyze the plurality of records. Person database entity 500 may also include one or more fields related to recording a history of changes and merges between records. Further, a functionality may exist in which person database entity 500 may be reverted back to a point in time before certain changes or merges took place. In some embodiments that are not shown in FIG. 5, person database entity may be a single reference record and accordingly may be represented by a single row of a database. The single reference record may include a field containing all of the record identifiers for all the records that have been merged into the person database entity.

Figure 6:
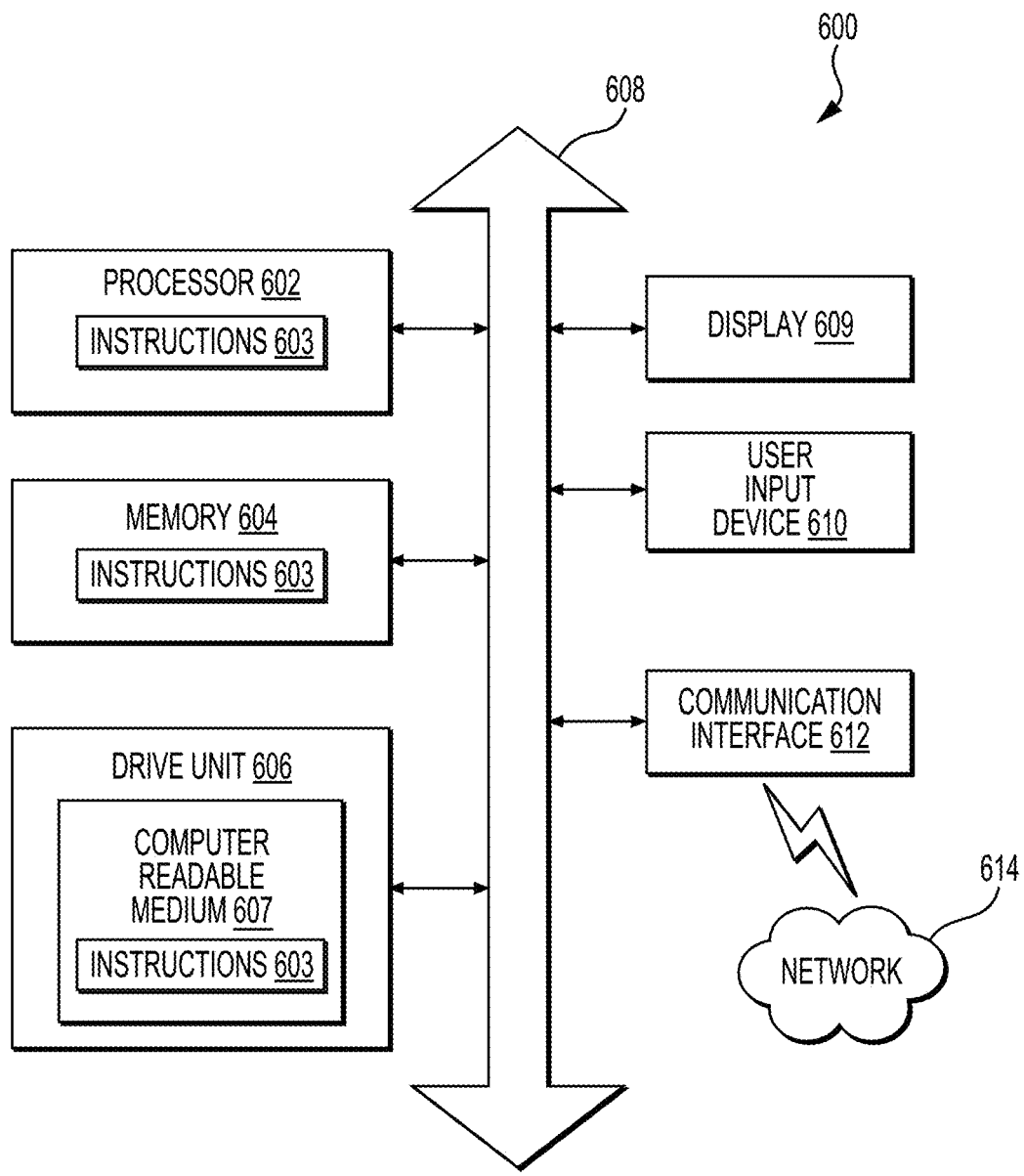
FIG. 6 illustrates an example computing device that may execute the techniques discussed herein.

FIG. 6 is a block diagram illustrating various example system components for use in accordance with the disclosed systems and methods. The computer system 600 includes a processor 602, e.g., a central processing unit (CPU), a graphics processing unit (GPU), or both. The processor 602 is a component in a variety of systems. For example, the processor 602 is part of a standard personal computer or a workstation. The processor 602 is one or more processors, digital signal processors, application specific integrated circuits, field programmable gate arrays, servers, networks, digital circuits, analog circuits, combinations thereof, or other now known or later developed devices for analyzing and processing data. The processor 602 implements a software program, such as code generated manually (i.e., programmed).

The computer system 600 includes a memory 604 that communicates via bus 608. Memory 604 is a main memory, a static memory, or a dynamic memory. Memory 604 includes, but is not limited to computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 604 includes a cache or random-access memory for the processor 602. In alternative implementations, the memory 604 is separate from the processor 602, such as a cache memory of a processor, the system memory, or other memory. Memory 604 is an external storage device or database for storing data. Examples include a hard drive, compact disc ("CD"), digital video disc ("DVD"), memory card, memory stick, floppy disc, universal serial bus ("USB") memory device, or any other device operative to store data. The memory 604 is operable to store instructions executable by the processor 602. The functions, acts, or tasks illustrated in the figures or described herein are performed by processor 602 executing the instructions stored in memory 604. The functions, acts, or tasks are independent of the particular type of instruction set, storage media, processor, or processing strategy and are performed by software, hardware, integrated circuits, firmware, micro-code, and the like, operating alone or in combination. Likewise, processing strategies include multiprocessing, multitasking, parallel processing, and the like.

As shown, the computer system 600 further includes a display 609, such as a liquid crystal display (LCD), an organic light emitting diode (OLED), a flat panel display, a solid-state display, a cathode ray tube (CRT), a projector, a printer or other now known or later developed display device for outputting determined information. The display 609 acts as an interface for the user to see the functioning of the processor 602, or specifically as an interface with the software stored in the memory 604 or in the drive unit 606.

Additionally or alternatively, the computer system 600 includes an input/output device 610 configured to allow a user to interact with any of the components of the computer system 600. The input/output device 610 is a number pad, a keyboard, a cursor control device, such as a mouse, a joystick, touch screen display, remote control, or any other device operative to interact with the computer system 600.

The computer system 600 also includes the drive unit 606 implemented as a disk or optical drive. The drive unit 606 includes a computer-readable medium 607 in which one or more sets of instructions 603, e.g. software, is embedded. Further, the sets of instructions 603 embodies one or more of the methods or logic as described herein. Instructions 603 resides completely or partially within memory 604 and/or within processor 602 during execution by the computer system 600. The memory 604 and the processor 602 also include computer-readable media as discussed above.

In some systems, computer-readable medium 607 includes the set of instructions 603 or receives and executes the set of instructions 603 responsive to a propagated signal so that a device connected to network 614 communicates voice, video, audio, images, or any other data over network 614. Further, the sets of instructions 603 are transmitted or received over the network 614 via the communication port or interface 612, and/or using the bus 608. The communication port or interface 612 is a part of the processor 602 or is a separate component. The communication port or interface 612 is created in software or is a physical connection in hardware. The communication port or interface 612 is configured to connect with the network 614, external media, display 609, or any other components in the computer system 600, or combinations thereof. The connection with network 614 is a physical connection, such as a wired Ethernet connection, or is established wirelessly as discussed below. Likewise, the additional connections with other components of the computer system 600 are physical connections or are established wirelessly. Network 614 alternatively be directly connected to the bus 608.

While the computer-readable medium 607 is shown to be a single medium, the term "computer-readable medium" includes a single medium or multiple media, such as a centralized or distributed database, and/or associated caches and servers that store one or more sets of instructions. The term "computer-readable medium" also includes any medium that is capable of storing, encoding, or carrying a set of instructions for execution by a processor or that causes a computer system to perform any one or more of the methods or operations disclosed herein. The computer-readable medium 607 is non-transitory, and may be tangible.

The computer-readable medium 607 includes a solid-state memory such as a memory card or other package that houses one or more non-volatile read-only memories. The computer-readable medium 607 is a random-access memory or other volatile re-writable memory. Additionally or alternatively, the computer-readable medium 607 includes a magneto-optical or optical medium, such as a disk or tapes or other storage device to capture carrier wave signals such as a signal communicated over a transmission medium. A digital file attachment to an e-mail or other self-contained information archive or set of archives is considered a distribution medium that is a tangible storage medium. Accordingly, the disclosure is considered to include any one or more of a computer-readable medium or a distribution medium and other equivalents and successor media, in which data or instructions are stored.

In an alternative implementation, dedicated hardware implementations, such as application specific integrated circuits, programmable logic arrays, and other hardware devices, is constructed to implement one or more of the methods described herein. Applications that include the apparatus and systems of various implementations broadly include a variety of electronic and computer systems. One or more implementations described herein implement functions using two or more specific interconnected hardware modules or devices with related control and data signals that are communicated between and through the modules, or as portions of an application-specific integrated circuit. Accordingly, the present system encompasses software, firmware, and hardware implementations.

Computer system 600 is connected to network 614. Network 614 defines one or more networks including wired or wireless networks. The wireless network is a cellular telephone network, an 802.11, 802.16, 802.20, or WiMAX network. Further, such networks include a public network, such as the Internet, a private network, such as an intranet, or combinations thereof, and utilizes a variety of networking protocols now available or later developed including, but not limited to TCP/IP based networking protocols. Network 614 includes wide area networks (WAN), such as the Internet, local area networks (LAN), campus area networks, metropolitan area networks, a direct connection such as through a Universal Serial Bus (USB) port, or any other networks that allows for data communication. Network 614 is configured to couple one computing device to another computing device to enable communication of data between the devices. Network 614 is generally enabled to employ any form of machine-readable media for communicating information from one device to another. Network 614 includes communication methods by which information travels between computing devices. Network 614 is divided into sub-networks. The sub-networks allow access to all of the other components connected thereto or the sub-networks restrict access between the components. Network 614 is regarded as a public or private network connection and includes, for example, a virtual private network or an encryption or other security mechanism employed over the public Internet, or the like.

While the foregoing has been described in conjunction with the example aspects outlined above and further described in the figures, various alternatives, modifications, variations, improvements, and/or substantial equivalents, whether known or that are or may be presently unforeseen, may become apparent to those having at least ordinary skill in the art. Accordingly, the exemplary aspects, as set forth above, are intended to be illustrative, not limiting. Various changes may be made without departing from the spirit and scope of the subject matter described herein. Therefore, aspects described herein intended to embrace all known or later-developed alternatives, modifications, variations, improvements, and/or substantial equivalents.

What is claimed is:

1. A computer-implemented method for merging records from a plurality of database systems, comprising:
    comparing, by one or more processors, two or more records of a plurality of records, wherein the plurality of records are from a plurality of database systems and each of the plurality of records is a patient record or an employee record;
    determining, by the one or more processors, that a threshold match exists between the two or more records based upon a set of threshold matching criteria;
    merging, by the one or more processors, the two or more records, based upon determining that the threshold match exists, into a person database entity, wherein a unique entity identifier is associated with the person database entity; and
    identifying, using the person database entity and the unique entity identifier, anomalous activity by a person associated with the person database entity based on activities associated with the two or more records.

2. The computer-implemented method of claim 1, wherein each record of the two or more records comprises one or more data points of demographic information, and wherein the threshold match exists when a threshold number of the one or more data points of demographic information of the two or more records match.

3. The computer-implemented method of claim 2, wherein the one or more data points of demographic information comprise at least one of a name, a date of birth, or a zip code.

4. The computer-implemented method of claim 1, wherein the set of threshold matching criteria comprises a number of one or more data points of demographic information that can be used to determine the threshold match at a particular confidence rate.

5. The computer-implemented method of claim 1, wherein the plurality of database systems are associated with a healthcare service provider.

6. The computer-implemented method of claim 1, wherein the plurality of database systems are associated with a plurality of healthcare service providers.

7. The computer-implemented method of claim 1, wherein merging the two or more records comprises storing a history of record changes and merges.

8. The computer-implemented method of claim 1, wherein the person database entity is associated with a set of records pertaining to a single person, the set of records including the two or more records.

9. The computer-implemented method of claim 8, wherein the single person is a patient and the set of records comprise a plurality of medical records.

10. The computer-implemented method of claim 8, wherein the single person is an employee and the set of records comprise a plurality of employee records.

11. The computer-implemented method of claim 8, wherein the single person is both a patient and an employee and the set of records comprise at least one patient record and at least one employee record.

12. The computer-implemented method of claim 8, further comprising:
determining, by the one or more processors and using a machine learning model, one or more anomalous activities based on data pertaining to the set of records.

13. The computer-implemented method of claim 12, wherein the one or more anomalous activities comprise:
unauthorized access to patient data; and/or
drug diversion activity.

14. The computer-implemented method of claim 1, wherein the unique entity identifier facilitates access to the person database entity by a plurality of platforms, each of the plurality of platforms configured to analyze the plurality of records.

15. The computer-implemented method of claim 1, further comprising updating, by the one or more processors at a second time, the person database entity, wherein the updating comprises:
adding a new record to the person database entity based upon determining that a second threshold match exists between the new record and the two or more records in the person database entity.

16. The computer-implemented method of claim 1, furthering comprising causing, by the one or more processors, a graphical user interface to be displayed on a computing device of a user for updating the person database entity, wherein the graphical user interface is configured to enable the user to at least one of:
add a new record to the person database entity using one or more first graphical elements of the graphical user interface; or
remove a record of the two or more records from the person database entity using one or more second graphical elements of the graphical user interface.

17. The computer-implemented method of claim 1, further comprising causing, by the one or more processors, a graphical user interface to be displayed on a computing device of a user, wherein the graphical user interface is configured to enable the user to at least one of:
select records to be merged into the person database entity independent of whether the threshold match exists between the records; or
select records to be not merged into the person database entity independent of whether the threshold match exists between the records.

18. A non-transitory computer readable medium storing instructions which, when executed by one or more processors, cause the one or more processors to perform operations for merging records from a plurality of database systems, comprising:
comparing two or more records of a plurality of records, wherein the plurality of records are from a plurality of database systems and each of the plurality of records is a patient record or an employee record;
determining that a threshold match exists between the two or more records based upon a set of threshold matching criteria;
merging the two or more records, based upon determining that the threshold match exists, into a person database entity, wherein a unique entity identifier is associated with the person database entity; and
using the person database entity and the unique entity identifier to identify anomalous activity by a person associated with the person database entity based on activities associated with the two or more records.

19. The non-transitory computer readable medium of claim 18, wherein each record of the two or more records comprises one or more data points of demographic information, and wherein the threshold match exists when a threshold number of the one or more data points of demographic information of the two or more records match.

20. A record consolidation system for merging records from a plurality of database systems, comprising:
a memory storing instructions; and
one or more processors operatively connected to the memory and configured to execute the instructions to perform operations including:
comparing two or more records of a plurality of records, wherein the plurality of records are from a plurality of database systems and each of the plurality of records is a patient record or an employee record;
determining that a threshold match exists between the two or more records based upon a set of threshold matching criteria;
merging the two or more records, based upon determining that the threshold match exists, into a person database entity, wherein a unique entity identifier is associated with the person database entity; and
using the person database entity and the unique entity identifier to identify anomalous activity by a person associated with the person database entity based on activities associated with the two or more records.

* * * * *